United States Patent
Ramella et al.

(10) Patent No.: US 9,956,326 B2
(45) Date of Patent: May 1, 2018

(54) PORTABLE SUCTION PUMP UNIT

(75) Inventors: Ivo Ramella, Ebikon (CH); Ignaz Henzen, Hagendorn (CH)

(73) Assignee: Medela Holding AG (CH)

( * ) Notice: Subject to any disclaimer, the term of this patent is extended or adjusted under 35 U.S.C. 154(b) by 365 days.

(21) Appl. No.: 13/885,490

(22) PCT Filed: Oct. 13, 2011

(86) PCT No.: PCT/CH2011/000243
§ 371 (c)(1),
(2), (4) Date: May 15, 2013

(87) PCT Pub. No.: WO2012/065274
PCT Pub. Date: May 24, 2012

(65) Prior Publication Data
US 2013/0237937 A1    Sep. 12, 2013

(30) Foreign Application Priority Data
Nov. 15, 2010  (CH) ..................... 1910/10

(51) Int. Cl.
*A61M 1/00*    (2006.01)

(52) U.S. Cl.
CPC ........ *A61M 1/0023* (2013.01); *A61M 1/0001* (2013.01); *A61M 1/0066* (2013.01); *A61M 2205/8206* (2013.01)

(58) Field of Classification Search
CPC ............ A61M 1/0001; A61M 39/1011; A61M 1/0023; A61M 1/0066; A61M 2205/8206
See application file for complete search history.

(56) References Cited

U.S. PATENT DOCUMENTS

| 5,645,540 A |   | 7/1997 | Henniges et al. |
| 5,807,359 A | * | 9/1998 | Bemis ................. A61M 1/0001 134/166 R |

(Continued)

FOREIGN PATENT DOCUMENTS

| EP | 1184043 A1 | 3/2002 |
| EP | 1679463 A1 | 7/2006 |

(Continued)

OTHER PUBLICATIONS

International Search Report for corresponding International App. No. PCT/CH2011/000243 dated Jan. 13, 2012.

*Primary Examiner* — Susan Su
*Assistant Examiner* — Kai Weng
(74) *Attorney, Agent, or Firm* — McDonnell Boehnen Hulbert & Berghoff LLP

(57) ABSTRACT

A portable suction pump unit for aspirating body fluids and/or air from a patient has a pump module housing for a pump module and a fluid collection container. The pump module housing has a pump-side suction connector, and the fluid collection container has a container-side suction connector for leaktight connection to the pump-side suction connector. The two suction connectors define a common axis. The fluid collection container can be secured on the pump module housing via a repeatedly releasable and restorable connection. This connection is releasable and/or restorable by means of a rotation movement of the fluid collection container relative to the pump module housing about said axis. The suction unit according to the invention is inexpensive to produce and permits an easily manageable connection between housing and container.

13 Claims, 4 Drawing Sheets

(56) References Cited

U.S. PATENT DOCUMENTS

2004/0122383 A1* 6/2004 Romano ............ A61M 1/0001
604/319
2008/0295847 A1* 12/2008 Gobel ................ A61M 39/1011
128/207.14
2009/0240218 A1 9/2009 Braga et al.
2010/0211030 A1 8/2010 Turner et al.

FOREIGN PATENT DOCUMENTS

| WO | 1999/10024 | 3/1999 |
| WO | 20071128156 | 11/2007 |

\* cited by examiner

PORTABLE SUCTION PUMP UNIT

CROSS-REFERENCE TO RELATED APPLICATIONS

This application claims the benefit of Swiss Patent Application No. 01910/10 filed Nov. 15, 2010, and International Patent Application No. PCT/CH2011/000243 filed Oct. 13, 2011, the contents of which are fully incorporated herein by reference.

TECHNICAL FIELD

The present invention relates to a portable suction pump unit, a fluid collection container and a pump module housing.

BACKGROUND

Stationary suction systems are normally used in the medical field to aspirate body fluids from body cavities or wounds. These suction systems generally comprise a suction source, in particular a vacuum pump, a fluid or secretion collection container, a surge tank arranged therebetween, and connection lines, in particular a drainage or secretion line leading from the patient to the fluid collection container, a connection line leading from the collection container to the surge tank, and a vacuum line connecting the surge tank to the suction source.

For the purposes of the healing process, it has now been found to be important for the patient to be able to move about unaided and leave bed as soon as possible. For this reason, portable suction systems of various designs have become known.

EP-A-1 184 043 discloses a miniature portable suction pump, in particular for wound drainage, which comprises an open collecting container for material that is to be aspirated, and a lid closing this container. All of the components necessary for the operation of the pump are integrated in the container lid.

WO 99/10024 describes a portable pump unit which is used for thorax drainage and which is connected via an external line to a likewise portable, kidney-shaped secretion collection container. This device has the disadvantage that two separate units have to be carried, which are also connected to each other by a hose.

WO 2007/128156 discloses a portable suction pump unit with a pump module housing and with a fluid collection container that can be secured thereon. This container is connected releasably to the housing by being held in corresponding guides of two protruding side walls of the housing. A drainage hose can, with its patient-side end designed as an adapter, be plugged into the housing and thus connected to the fluid collection container.

US 2010/0211030 describes a small portable wound drainage pump with a pump module housing and with a fluid collection container that can be secured thereon. They are secured by catches.

Some of these suction pump units have proven useful in practice. However, tipping movements, when the fluid collection container is too full, can lead to contamination of the environment.

Moreover, the filled fluid collection containers can often be detached from the pump module only with difficulty, since in most cases there is still a low underpressure present in the container. Considerable force therefore has to be applied in order to release the connection.

Moreover, the fluid collection containers are designed to be disposed of after use, and they are usually discarded together with their contents. It is therefore essential that they are produced as inexpensively as possible.

SUMMARY

It is therefore an object of the invention to make available a portable suction pump unit whose fluid collection container is inexpensive to produce and in which the connection between container and pump module is easy to establish and release.

The portable suction pump unit according to the invention for aspirating body fluids and/or air from a patient has a pump module housing for a pump module and a fluid collection container. The pump module housing has a pump-side suction connector, and the fluid collection container has a container-side suction connector for leaktight connection to the pump-side suction connector. The two suction connectors define a common axis. The fluid collection container can be secured on the pump module housing via a repeatedly releasable and restorable connection. In one aspect, this connection is releasable and/or restorable by means of a rotation movement of the fluid collection container relative to the pump module housing about said common axis.

Here, rotation movement is also understood as meaning rotations of less than or equal to 360°, that is to say actual pivoting movements about the axis. Rotation can in particular be effected by an angle of approximately 90° or approximately 45°, until an abutment is reached.

By virtue of the rotation movement about the common axis of the suction connectors, a tilting movement is avoided when establishing and/or releasing the connection between fluid collection container and pump module housing. In this way, the fluid collection container can be removed without the liquid located therein sloshing around too much and, in the worst case, even escaping from the container.

The connection between suction pump and container, i.e. the suction line connecting the parts, is preferably established at the same time as the connection between housing and container. That is to say, when the end position of the relative rotation between housing and container is reached, a leaktight suction line is established and the device is ready for operation. No other suction lines, in particular no external suction lines, are needed between housing and container. The fluid collection container is in this way arranged very close on the pump module, which optimizes the functioning of the unit.

By virtue of the rotation movement, the container, even when there is a residual vacuum therein, can be released from the pump module housing easily and by application of a slight force.

The axis, in correct use of the suction pump unit, is preferably a vertical axis.

In one example embodiment, the fluid collection container, in the correct position of use, is arranged under the pump module housing, wherein the pump-side suction connector is arranged in a base of the pump module housing, and the container-side suction connector is arranged in a lid of the fluid collection container. This has the advantage that the fluid is collected at the lowest point of the device.

The container-side suction connector and/or the pump-side suction connector can be arranged along the longitudinal centre axis of the container and of the housing, respectively. However, they can also be arranged offset from the centre.

The lid of the fluid collection container is preferably formed in one piece with the rest of the fluid collection container or is welded or adhesively bonded thereto. In particular, the fluid collection container is completely closed, except for the container-side suction connector and another, patient-side suction connector. The container is therefore closed, even after its removal from the pump module housing, and accidental escape of the fluid is avoided.

In the solution according to one aspect, there are no complicated catches or other fixing elements to be secured on the container and on the housing.

In one example embodiment, fixing elements are present in order to fix the two connection parts, i.e. fluid collection container and pump module housing, relative to each other in a correct position of use. These fixing elements may be integral components of the housing and/or of the container. This simplifies production and reduces costs.

In one example embodiment, these fixing elements are formed by a hollow pin with an outer thread and by a recess with an inner thread for receiving the pin. In one variant, the hollow pin is arranged in the pump module housing and the recess is arranged in the fluid collection container, wherein the container-side suction connector is located in the recess and the pump-side suction connector is located in the pin. The arrangement can also be exactly the other way round, i.e. the pin in the fluid collection container, and the recess in the housing. The leaktight suction connection between pump and container is thus established in a simple way, with this connection being established together with the establishment of the connection between housing and container. Instead of such a connection, it is also possible to use a bayonet catch for example. The nature of the connection between housing and container can vary, provided that it permits a rotation movement.

In one example embodiment, both connection parts have locking elements or abutment elements, wherein these locking elements or abutment elements are each arranged on a circle. These circles each have a centre point that lies on the axis. This arrangement ensures an exact positioning and a defined rotation as far as an abutment. These locking elements may permit the correct fitting of the fluid collection container on the housing in only a single rotation position. However, it is also possible, for example, to permit a maximum of two rotation positions or another number of rotation positions.

In one example embodiment, the locking elements or abutment elements of one of the connection parts are designed as grooves which curve along a circle and at each of whose ends a first locking point is present, and wherein the locking elements or abutment elements of the other connection part are designed as guide blocks which curve along a circle of the same size and at each of whose ends there is a second locking point. The locking points can be dimples and matching elevations or lugs. It is also possible, for example, to use magnets.

The container-side suction connector and/or the pump-side suction connector may be designed with a sealing element for establishing the leaktight connection.

In one example embodiment, the pump-side suction connector is designed as an insert part which passes through an opening of the pump module housing. The leaktightness of the suction line can easily be ensured in this way. Moreover, this insert part can be designed as a replacement part such that it can be exchanged after a certain number of connections have been established, in order to ensure the leaktightness over a long period of time.

In one example embodiment, the fluid collection container and the pump module housing, at least in the area of their connection, each have a contour of the same shape and size and are thus flush with each other when the connection is established. In one example embodiment, they have an approximately oval or kidney-shaped cross section, at least in the area of their connection.

Other embodiments are set forth in the dependent claims.

BRIEF DESCRIPTION OF THE DRAWINGS

Preferred embodiments of the invention are described below with reference to the drawings, which serve only for explanatory purposes and are not to be interpreted as limiting the invention. In the drawings.

Identical parts are provided with identical reference signs.

DETAILED DESCRIPTION

A first illustrative embodiment of a suction pump unit according to the invention is shown in FIGS. 1 to 7. It principally comprises a pump module housing 1 and, arranged on the latter, a fluid collection container 2. Housing 1 and fluid collection container 2 are preferably made of plastic, and at least the fluid collection container 2 is preferably transparent.

The fluid collection container 2 has stiff walls and is therefore dimensionally stable. Preferably, all of its walls are stiff. It has a patient-side suction connector 20. In this example, the latter is a hollow cylindrical or frustoconical stub for receiving a suction hose. The container 2 may have a substantially cylindrical outer basic shape. Its cross section is preferably oval or kidney-shaped. The top face and bottom face may extend parallel to each other. The top face, i.e. the lid, is likewise substantially plane. The deviations from this plane are described in more detail below. The container 2 is preferably closed, except for said patient-side suction connector 20 and a container-side suction connector 22. The container 2 is preferably designed in one piece or welded or adhesively bonded. In particular, the lid preferably cannot be removed from the rest of the container without being destroyed.

Figure 6:
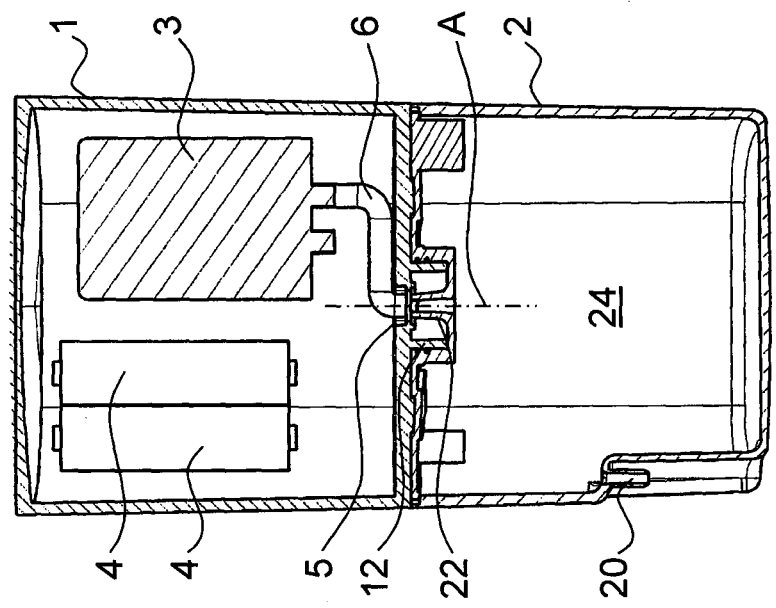
FIG. 6 shows a longitudinal section through the unit according to FIG. 1, along a first plane.

The pump module housing 1 serves to accommodate an electric, motor-driven suction pump 3 and all of the components necessary for operating the suction pump 3. The housing 1 has a display 11 and at least one, preferably several control elements 10. The control elements 10 are, for example, keys, touch-sensitive panels or rotary knobs. A power supply connection 14 is also provided on the housing 1 for connecting the suction pump 3 to an electricity supply network. The interior of the pump module housing 1 accommodates, as can be seen in FIG. 6, said suction pump 3 and preferably one or more batteries 4. As can be seen from FIG. 7, the electronics for controlling the pump 3 are also arranged in the interior of the housing 1. Here, a circuit board 100 is shown as representative of all other possible electronic components.

The pump module housing 1 also preferably has a substantially cylindrical outer shape. Its cross section is preferably likewise oval or kidney-shaped. The pump module housing 1 has a substantially flat base which, in correct use, faces the fluid collection container 2 and makes contact with the latter. At least in the area of contact with the fluid collection container 2, the outer shape of the pump module housing 1 corresponds both in shape and size to the configuration of the fluid collection container 2. In this way, the side walls of both parts are substantially flush, as can be clearly seen in FIG. 1.

Figure 3:
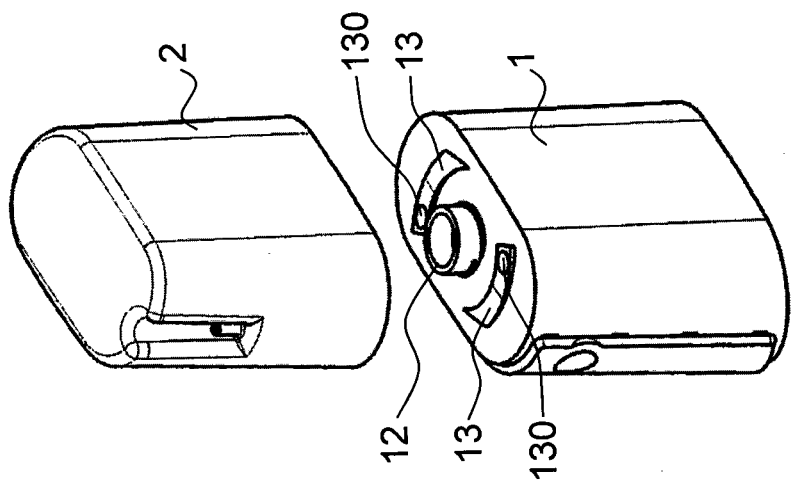
FIG. 3 shows the suction pump unit according to FIG. 2 inverted and standing on its head.
Figure 2:
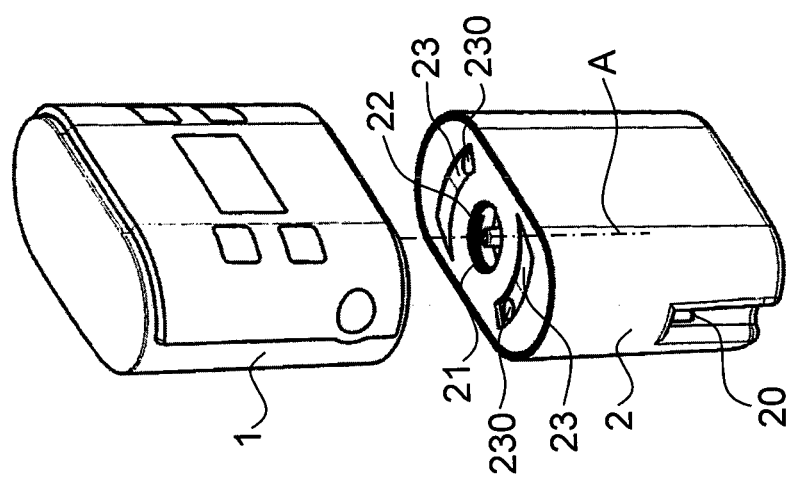
FIG. 2 shows the suction pump unit according to FIG. 1 with the fluid collection container and pump module housing released from each other.
Figure 1:
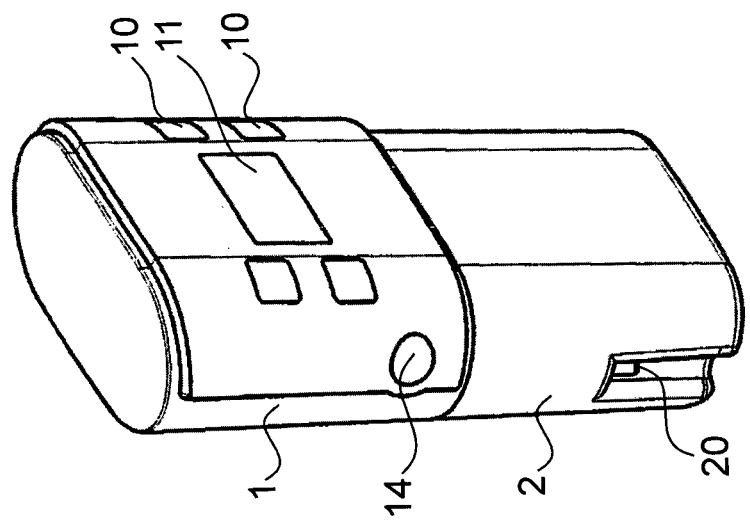
FIG. 1 shows a schematic perspective view of a suction pump unit according to the invention in a first illustrative embodiment.
Figure 5:
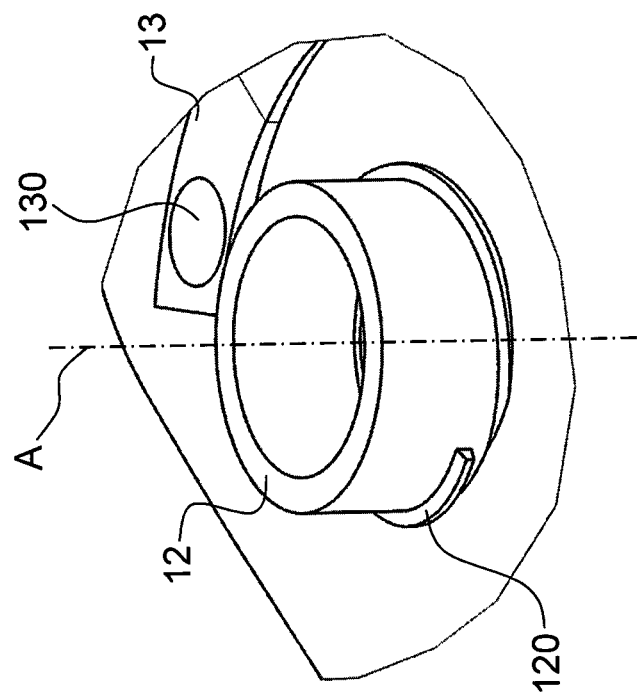
FIG. 5 shows an enlarged detail, according to FIG. 3, of the pump module housing in the area of the pump-side suction connector.
Figure 4:
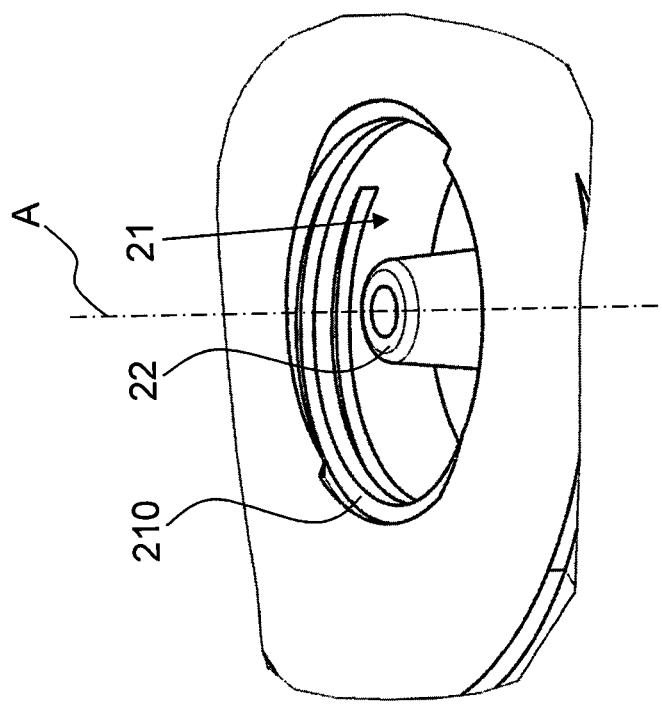
FIG. 4 shows an enlarged detail, according to FIG. 2, of the fluid collection container in the area of the container-side suction connector.
Figure 7:
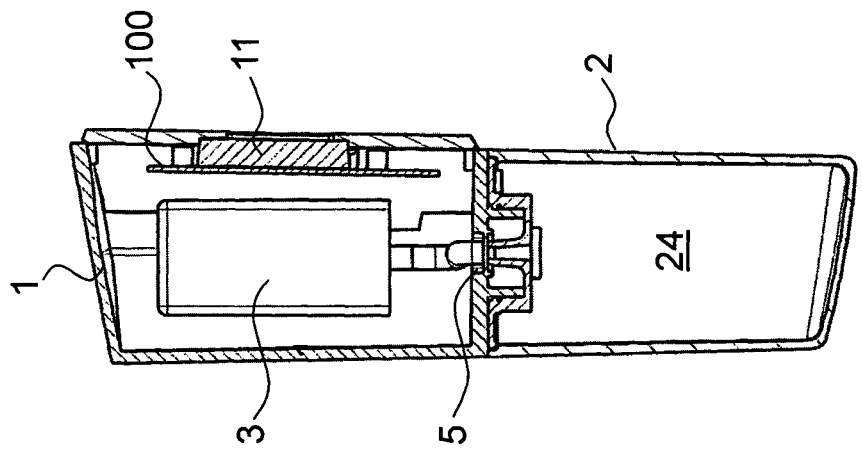
FIG. 7 shows a longitudinal section through the unit according to FIG. 1, in a second plane at right angles to the first plane.

The pump module housing 1 has a container-side suction connector 5, which is connected to the suction pump 3 via an internal suction line 6 running in the housing 1. This is shown in FIGS. 5 and 6. This pump-side suction connector 5 ends in a pin 12 protruding downwards from the base of the housing 1. The suction connector 5 itself can be formed by a simple opening in the base of the housing 1. However, it can also itself form an outwardly and/or inwardly protruding stub. The pin 12 has a hollow cylindrical shape and protects the pump-side suction connector 5 from the effect of external forces and from contamination. The pin 12 can be seen clearly in FIGS. 3 and 5.

Matching this pin 12 and the pump-side suction connector 5, the fluid collection container 2 has the container-side suction connector 22, which is arranged in a recess 21 in the lid. The width and depth of the recess 21 are designed to receive the pin 12. The container-side suction connector 22 is formed by a stub protruding from the base of the depression 21. It engages in the pump-side suction connector 5 and forms, with the latter, a leaktight connection of the suction line 6 to a hollow space 24 of the fluid collection container 2. In this way, a longitudinal axis A is also defined, which in this example also corresponds to the vertical axis of the unit.

The pin 12 is provided with an outer thread 120, and the recess 21 is provided with an inner thread 210 meshing with said outer thread 120. In this way, the two suction connectors 5, 22 can be easily connected to each other in an exact position, the threads allowing the container 2 to be fixed with respect to the housing 1.

Moreover, the unit preferably has locking elements or abutments, which permit an exact positioning and a defined rotation of the connection parts, i.e. of the housing 1 and of the container 2, relative to each other. In this example, these are slits or guide grooves 23 and groove or guide blocks 13, which each curve along a respective circle and match each other in shape and size. These locking elements can be seen clearly in FIGS. 2 and 3. In this example, the container 2 has the recessed grooves 23, and the housing 1 has the guide blocks 13. However, these can also be arranged the other way around, with the container 2 having the guide blocks 13 and the housing 1 having the recessed grooves 23.

The grooves 23 and guide blocks 13 each curve along a respective circle and each form a section of a circle. The circles are the same size, and their centre points lie on the axis A, i.e. the vertical axis of the unit.

In this example, there are two grooves 23 lying opposite each other and two guide blocks 13 lying opposite each other. However, it is also possible for just one of each element to be present, or three or more such elements.

In each groove 23, there is a raised locking lug 230, which is arranged at the end of the groove in the direction of rotation. Each guide block 13 has, at a corresponding position, a recessed locking dimple 130 into which the respective locking lug 230 locks in the end position, i.e. in the correct position of use. The locking lug 230 and the locking dimple 130 are sufficiently flexible to ensure that this connection can be released again without destruction, by rotation in the opposite direction with application of a slight additional force. Instead of the locking lug 230 and the locking dimple 130, magnets can also be arranged at these locations, such that the locking action takes place magnetically. At their other end, the groove 23 and the guide block 13 are preferably widened, in order to make it easier to join housing 1 and container 2 together.

The container 2 can in this way be easily released from the housing 1 and connected thereto again. This can be done several times without destruction, and with the leaktightness of the suction connection being restored in each case.

Figure 8:
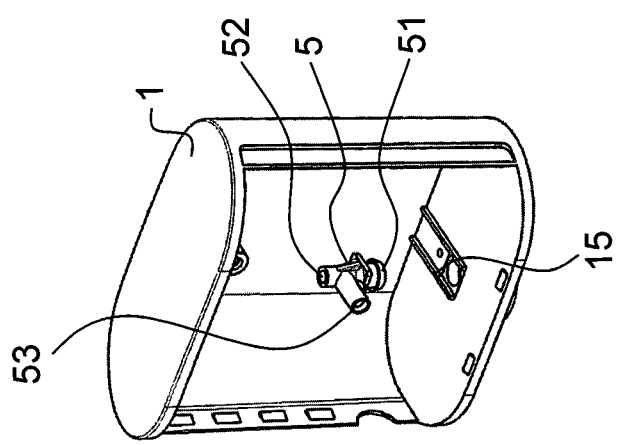
FIG. 8 shows a schematic view of the interior of a substantially empty pump module housing, with a pump-side suction connector according to a second embodiment.

FIG. 8 shows a second embodiment. Here, the pump-side suction connector 5 is designed as a separate component, in particular as an injection-moulded part. It is inserted into the base of the housing 1, with sealing rings on the housing 1 and/or on the insert part 5 ensuring a leaktight connection to the housing 1. The insert part has an outwardly directed connector stub 51 for connection to the container-side suction connector 22. An inwardly directed line connector 52 serves for connection to the internal suction line 6. A third stub 53 serves as a connector for a sensor, for example an underpressure sensor.

Figure 10:
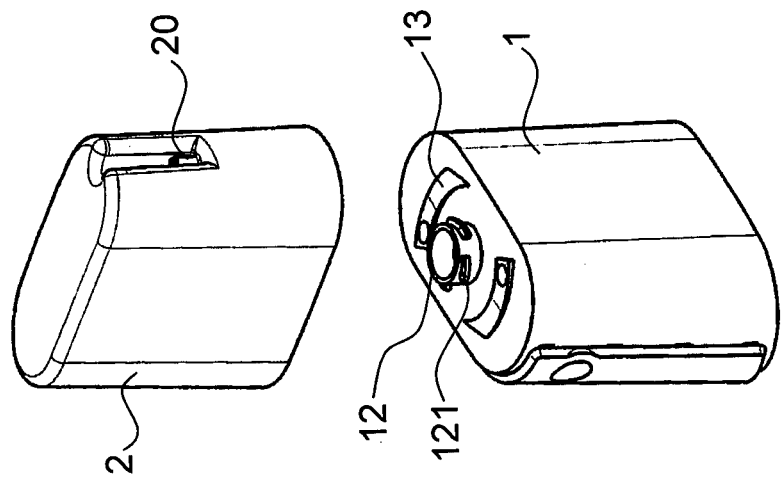
FIG. 10 shows the suction pump unit according to FIG. 9 inverted and standing on its head.
Figure 9:
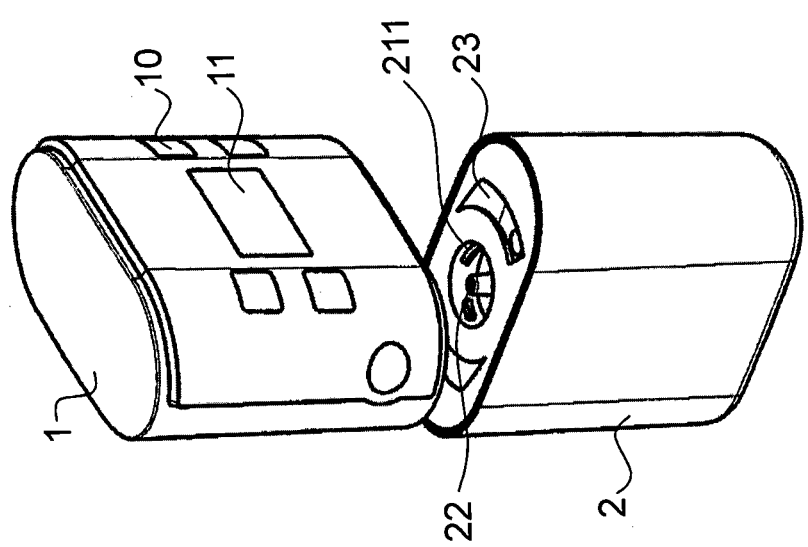
FIG. 9 shows a schematic view of a suction pump unit according to the invention with the pump module housing and fluid collection container released from each other in a third embodiment.

FIGS. 9 and 10 also show another kind of fixing means. Here, instead of the continuous outer thread and inner thread according to the first example, an interrupted outer thread 121 and interrupted inner thread 211 are shown.

The suction unit according to the invention is inexpensive to produce and permit an easily manageable connection between housing and container.

The invention claimed is:

1. A portable suction pump unit for aspirating body fluids, air or both body fluids and air from a patient, comprising:
   a fluid collection container and
   a pump module housing for a pump module, wherein the pump module housing has a pump-side suction connector, wherein the fluid collection container has a container-side suction connector for leaktight connection to the pump-side suction connector, wherein the two suction connectors define a common axis,
   wherein the fluid collection container can be secured on the pump module housing via a repeatedly releasable and restorable connection, wherein this connection is releasable and/or restorable by means of a rotation movement of the fluid collection container relative to the pump module housing about said axis,
   wherein fixing elements are present to fix the fluid collection container and the pump module housing relative to each other in a position for use, and wherein the fixing elements are a hollow pin with an outer thread and a recess with an inner thread for receiving the pin, wherein the hollow pin is arranged in the pump module housing and the recess is arranged in the fluid collection container, wherein the container-side suction connector is located in the recess and the pump-side suction connector is located in the pin or wherein the hollow pin is arranged in the fluid collection container and the recess is arranged in the pump module housing, wherein the pump-side suction connector is located in the recess and the container-side suction connector is located in the pin, wherein, by means of the rotation movement, the leaktight connection of the container-side suction connector to the pump-side suction connector is established at the same time as the fixation of the fluid collection container and the pump module housing, wherein the fluid collection container and the pump module housing each have at least one locking element or abutment element to ensure an exact positioning and a defined rotation of the fluid collection container relative to the pump module housing as far as an abutment, and wherein the locking elements or abutment elements of one of the connection parts includes at least one guide groove that curves along a circle and has a first locking point at an end of the at least one guide groove, and wherein the locking elements or abutment elements of the other connection part includes at least one guide block that curves along a circle of the same size and has a second locking point at an end of the at least one guide block that corresponds to a position of the first locking point to engage in operative connection with the first locking point, wherein both circles have a center point that lies on the axis.

2. The suction pump unit according to claim 1, wherein the fluid collection container is arranged under the pump module housing, wherein the fluid collection container has a lid and the pump module housing has a base, wherein the pump-side suction connector is arranged in the base of the pump module housing, and the container-side suction connector is arranged in the lid of the fluid collection container.

3. The suction pump unit according to claim 1, wherein the fluid collection container is completely closed, except for the container-side suction connector and another, patient-side suction connector.

4. The suction pump unit according to claim 1, wherein the rotation movement is less than or equal to 360°.

5. The suction pump unit according to claim 1, wherein the axis, during correct use of the suction pump unit, is at least approximately a vertical axis.

6. The suction pump unit according to claim 2, wherein the fluid collection container has a top face formed by the lid and a bottom face, wherein the base of the pump module housing is substantially flat, and wherein the top face and the bottom face of the fluid collection container extend parallel to each other.

7. The suction pump unit according to claim 6, wherein the lid of the fluid collection container is formed in one piece with the rest of the fluid collection container or is welded or adhesively bonded thereto.

8. The suction pump unit according to claim 2, wherein the fluid collection container has a top face formed by the lid and a bottom face, wherein the base of the pump module housing is substantially flat, and wherein the top face and the bottom face of the fluid collection container extend parallel to each other.

9. The suction pump unit according to claim 1, wherein the pump-side suction connector is designed as an insert part, which passes through an opening of the pump module housing.

10. The suction pump unit according to claim 1, wherein the container-side suction connector and/or the pump-side suction connector is designed with a sealing element for establishing the leaktight connection.

11. The suction pump unit according to claim 1, wherein the fluid collection container and the pump module housing, at least in the area of their connection, each have a contour of the same shape and size and are thus flush with each other when the connection is established.

12. A fluid collection container for use in a suction pump unit claim 1, comprising:

a container-side suction connector for leaktight connection to a pump module housing, such that an under-pressure can be generated in the fluid collection container by means of a pump module arranged in the pump module housing, wherein this suction connector has a longitudinal center axis, and wherein the fluid collection container has a fixing element on the fluid collection container side, which fixing element permits a repeatedly releasable and restorable fixation of the fluid collection container and the pump module housing relative to each other in a position for use, wherein the fixing element is a hollow pin with an outer thread or a recess with an inner thread, wherein the container-side suction connector is located in the recess or in the pin, wherein the suction connector on the fluid collection container side and the fixing element on the fluid collection container side are designed and are arranged relative to each other in such a way that, by means of a rotation movement of the fluid collection container relative to the pump module housing about the longitudinal center axis, the leaktight connection via the container-side suction connector to the pump module housing is established at the same time as the repeatedly releasable and restorable fixation of the fluid collection container and the pump module housing, wherein the fluid collection container has at least one locking element or abutment element that, in combination with a respective locking element or abutment element of the pump module housing, ensures an exact positioning and a defined rotation of the fluid collection container relative to the pump module housing as far as an abutment.

13. A pump module housing for use in a suction pump unit according to claim 1, comprising:

a pump-side suction connector for leaktight connection to a fluid collection container, such that an under-pressure can be generated in the fluid collection container by means of a pump module arranged in the pump module housing, wherein this suction connector has a longitudinal center axis, and wherein the pump module housing has a pump-side fixing element, which permits a repeatedly releasable and restorable fixation of the pump module housing and the fluid collection container relative to each other in a position for use, wherein the pump-side suction connector and the pump-side fixing element are designed and are arranged relative to each other in such a way that, by means of a rotation movement of the fluid collection container relative to the pump module housing about the longitudinal center axis, the leaktight connection via the pump-side suction connector to the fluid collection container is established at the same time as the repeatedly releasable and restorable fixation of the pump module housing and the fluid collection container relative to each other via the pump-side fixing element, wherein the pump module housing has a base, and wherein the pump-side suction connector is arranged in the base of the pump module housing.

\* \* \* \* \*